(12) United States Patent
Ono

(10) Patent No.: US 6,535,757 B2
(45) Date of Patent: Mar. 18, 2003

(54) OCULAR EXAMINATION SYSTEM

(75) Inventor: Shigeaki Ono, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 33 days.

(21) Appl. No.: 09/887,114

(22) Filed: Jun. 25, 2001

(65) Prior Publication Data

US 2002/0008848 A1 Jan. 24, 2002

(30) Foreign Application Priority Data

Jul. 19, 2000 (JP) ....................................... 2000-218341

(51) Int. Cl.[7] ............................................. A61B 3/10
(52) U.S. Cl. ...................... 600/476; 351/210; 351/221
(58) Field of Search ............................ 6700/476, 310; 351/209, 210, 221; 356/345

(56) References Cited

U.S. PATENT DOCUMENTS

| | | | |
|---|---|---|---|
| 5,106,184 A | 4/1992 | Milbocker | 351/221 |
| 5,894,337 A | 4/1999 | Okinishi et al. | 351/205 |
| 6,192,269 B1 | 2/2001 | Okumura et al. | 600/479 |
| 6,332,683 B1 * | 12/2001 | Ono et al. | 351/210 |
| 6,337,993 B1 * | 1/2002 | Kishida et al. | 600/476 |
| 2001/0056239 A1 * | 12/2001 | Ono | 600/476 |
| 2002/0058874 A1 * | 5/2002 | Ono et al. | 600/476 |

FOREIGN PATENT DOCUMENTS

| | | |
|---|---|---|
| JP | 63-288133 | 11/1988 |
| JP | 6-503733 | 4/1994 |
| JP | 7-31596 | 2/1995 |

* cited by examiner

Primary Examiner—Shawna J Shaw
(74) Attorney, Agent, or Firm—Fitzpatrick, Cella, Harper & Scinto

(57) ABSTRACT

An ocular examination system includes an illumination system illuminating a region of an eye fundus including a target blood vessel and adjusting the intensity of light illuminating the region, an image pickup device receiving light scattered from the region and producing signals in response to receiving the scattered light from the region, a control system receiving the signals and computing the diameter of the target blood vessel based on the signals, and a tracking system performing an automatic tracking operation on the target blood vessel based on the signals. The control system controls the illumination system to increase the intensity of the illumination applied to the region when the automatic tracking operation and the target-blood-vessel-diameter computation are simultaneously performed above the level of the illumination applied to the region when the automatic tracking operation is performed while the target-blood-vessel-diameter computation is not performed.

36 Claims, 8 Drawing Sheets

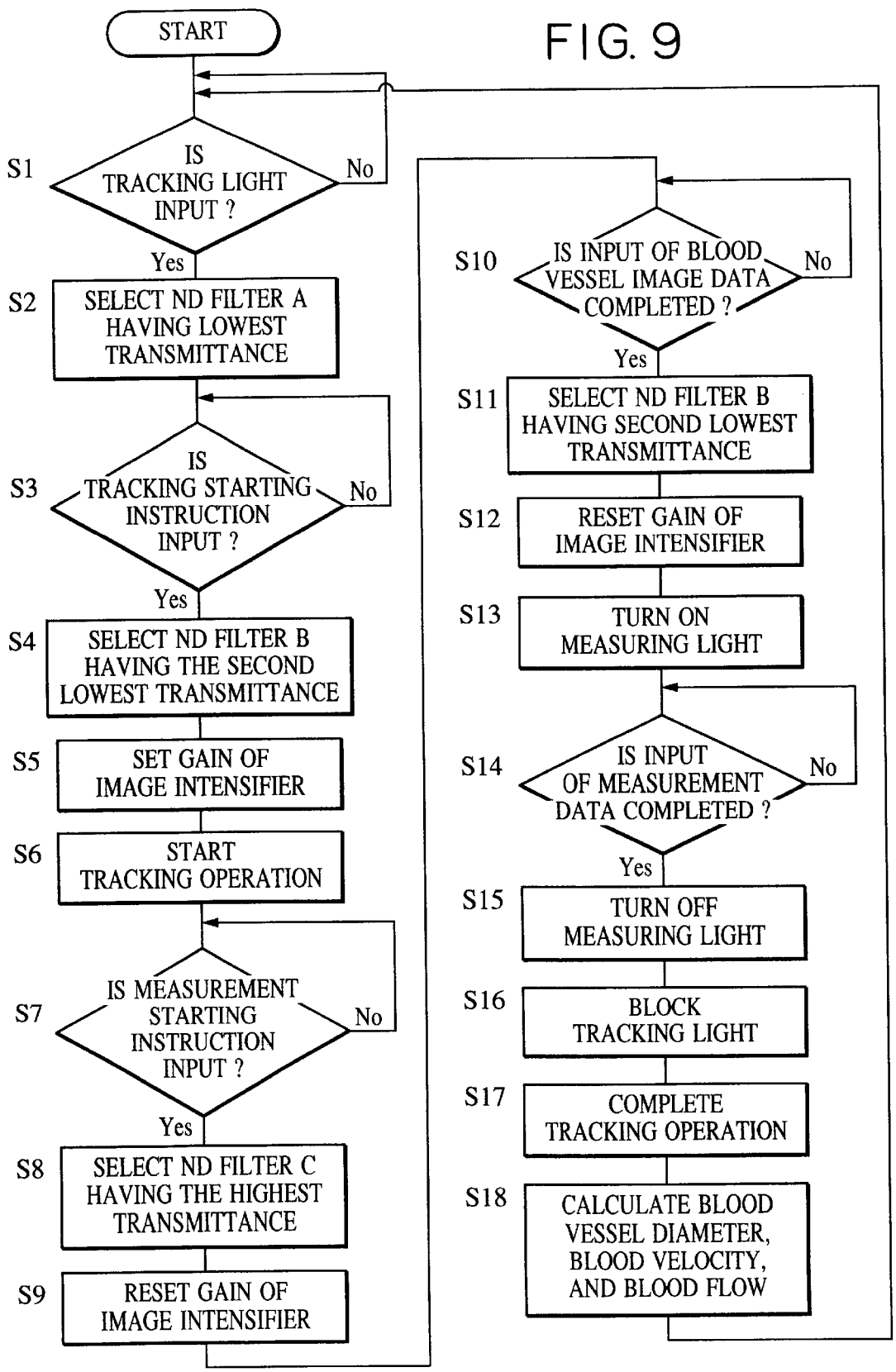

OCULAR EXAMINATION SYSTEM

BACKGROUND OF THE INVENTION

1. Field of the Invention

The present invention generally relates to an ocular examination system for examining the blood vessels of an eye fundus.

2. Description of the Related Art

The principle of a measurement operation performed by a retinal blood flow meter, which is an example of an ocular examination system, is discussed below. A laser beam having a wavelength $\lambda$ is applied to a subject blood vessel of a patient's eye, and the light scattered and reflected by the blood vessel is received by a photodetector. Then, an interference signal of a Doppler shift component, i.e., the light scattered and reflected by the blood moving in a blood vessel and the light scattered and reflected by a stationary blood vessel wall is detected. Upon analyzing the frequency of the interference signal, the blood velocity is determined. More specifically, the blood velocity, i.e., the maximum $V_{max}$, is determined according to the following equation:

$$V_{max} = \{\lambda/(n \cdot \alpha)\} \cdot \|\Delta f_{max1}| - |\Delta f_{max2}\|/\cos \beta \qquad (1)$$

wherein $\Delta f_{max1}$ and $\Delta f_{max2}$ indicate the maximum frequency shifts calculated from the received-light signals received by two photodetectors; $\lambda$ represents the wavelength of the laser light; n designates the index of refraction of a portion of the eye to be examined; a indicates the angle between the two light-detecting optical axes within the eye; and $\beta$ represents the angle between the plane formed by the two light-detecting optical axes and the velocity vector of the blood flow.

By measuring the blood velocity from the two directions as discussed above, contributions due to the directions of incidence of the measuring beams are canceled, thereby making it possible to measure the velocity of blood at a certain portion on the eye fundus. By matching the line of intersection between the plane formed by the two light-detecting optical axes and the eye fundus to the angle $\beta$, $\beta$ becomes 0 degrees, thereby measuring the true maximum velocity.

According to the retinal blood flow meter for measuring the shape of a blood vessel or the blood velocity in a blood vessel in a particular portion of the eye fundus by utilizing the laser beam, it is necessary that a beam of measuring light is precisely applied to a subject portion for a predetermined period. In actuality, however, it is difficult to precisely keep applying the measuring light to the subject portion due to involuntary eye movement. In order to solve this problem, an ocular system provided with a tracking function for detecting the position of a blood vessel and moving the measuring light to the subject portion in accordance with involuntary eye movement in real time is disclosed in Japanese Patent Laid-open Nos. 63-288133 and 6-503733 (by PCT).

In the above-described ocular system, the tracking operation is performed as follows. A linear charge-coupled device (CCD) is used for applying a beam of tracking light to an eye fundus and for receiving light reflected by the eye fundus and producing a blood-vessel-image signal. Then, the waveform of the blood-vessel-image signal is processed so as to calculate the amount of movement of the blood-vessel image from a tracking reference position. Tracking light emitted from a tracking illumination light source and measuring light are applied to an eye fundus via a pupil conjugate mirror, and the linear CCD is used for receiving the light reflected by the eye fundus so as to process the waveform of the blood-vessel-image signal. A system for calculating a blood-vessel diameter by using a blood-vessel-image signal output from a linear CCD is disclosed in Japanese Patent Laid-open No. 7-31596.

However, the above-described ocular examination systems have to perform a tracking operation while following the fast eye movement, and thus, a sufficient accumulation time of the linear CCD cannot be ensured. Accordingly, in order to obtain a blood-vessel image having a sufficient amplitude for performing the tracking operation and for calculating the blood-vessel diameter, an image intensifier is used for performing light amplification. However, with an excessively high amplification factor, the signal-to-noise (S/N) ratio of the blood-vessel-image signal from the linear CCD is reduced, thereby resulting in the lowered measurement precision of the blood-vessel diameter.

This problem may be solved by removing unwanted high-frequency noise components by performing filtering processing. However, since various diameters of blood vessels are measured, the feature points for calculating the blood-vessel diameter may inconveniently be removed together with the noise components depending on the setting of the cut-off frequency. Alternatively, the intensity of tracking light applied to a patient's eye fundus may be uniformly increased so as to reduce the amplification factor of the image intensifier, thereby suppressing noise components. In the aforementioned ocular examination systems, however, the maximum permissible exposure (MPE), which is the maximum permissible laser energy to be applied to a patient's eye, is set by the American National Standard Institute (ANSI) for the safety of the patients. Accordingly, measuring light is applied to a patient's eye without exceeding the MPE, resulting in a limitation on the number of measurements for the same subject portion of the eye.

SUMMARY OF THE INVENTION

Accordingly, a major object of the present invention is to improve a conventional ocular examination system. More specifically, it is an object of the present invention to achieve high-precision ocular examination by applying light to an eye fundus at a suitable intensity level.

It is another object of the present invention to achieve high-precision ocular examination without restricting the number of measurements for the same subject portion of the eye.

In order to achieve the above objects, according to the present invention, there is provided an ocular examination system comprising an illumination system configured to illuminate a region of an eye fundus of an eye including a target blood vessel, the illumination system being configured to adjust the intensity of light illuminating the region, an image pickup device positioned and configured to receive light scattered from the region illuminated by the illumination system and to produce signals in response to receiving the scattered light from the region, a control system connected to the illumination system and the image pickup device so as to receive the signals produced by the image pickup device and configured to compute the diameter of the target blood vessel based on the signals from the image pickup device, and a tracking system connected to the control system and configured to perform an automatic tracking operation on the target blood vessel based on the signals from the image pickup device. The control system is configured to control the tracking system so that the tracking system performs the automatic tracking operation simultaneous with the control system computing the diameter of the target blood vessel and so that the tracking system performs the automatic tracking operation when the control system does not computer the diameter of the target blood vessel. The control system is also configured to control the illumination system to change the intensity of the illumination applied to the region when the automatic tracking operation and the target-blood-vessel-diameter computation are simultaneously performed above the level of the illumination applied to the region when the automatic tracking operation is performed while the control system does not compute the target-blood-vessel diameter.

According to another aspect, the present invention that achieves these objectives relates to an ocular examination system comprising illumination means for illuminating a region of an eye fundus of an eye including a target blood vessel and for adjusting the intensity of light illuminating the region, image pickup means for receiving light scattered from the region illuminated by the illumination means and for producing signals in response to receiving the scattered light from the region, control means for computing the diameter of the target blood vessel based on the signals from the image pickup means, and tracking means for performing an automatic tracking operation on the target blood vessel based on the signals from the image pickup means. The control means comprises means for controlling the tracking means so that the tracking means performs the automatic tracking operation simultaneous with the control means computing the diameter of the target blood vessel and so that the tracking means performs the automatic tracking operation when the control means does not compute the diameter of the target blood vessel. The control means also comprises means for controlling the illumination means to change the intensity of the illumination applied to the region when the automatic tracking operation and the target-blood-vessel-diameter computation are simultaneously performed above the level of the illumination applied to the region when the automatic tracking operation is performed while the control means does not compute the target-blood-vessel diameter.

Further objects, features and advantages of the present invention will become apparent from the following description of the preferred embodiments with reference to the attached drawings.

BRIEF DESCRIPTION OF THE DRAWINGS

FIG. 9 is a flow chart illustrating the operation of the modification using the ND filter unit shown in FIG. 8.

DESCRIPTION OF THE PREFERRED EMBODIMENTS

Figure 1:
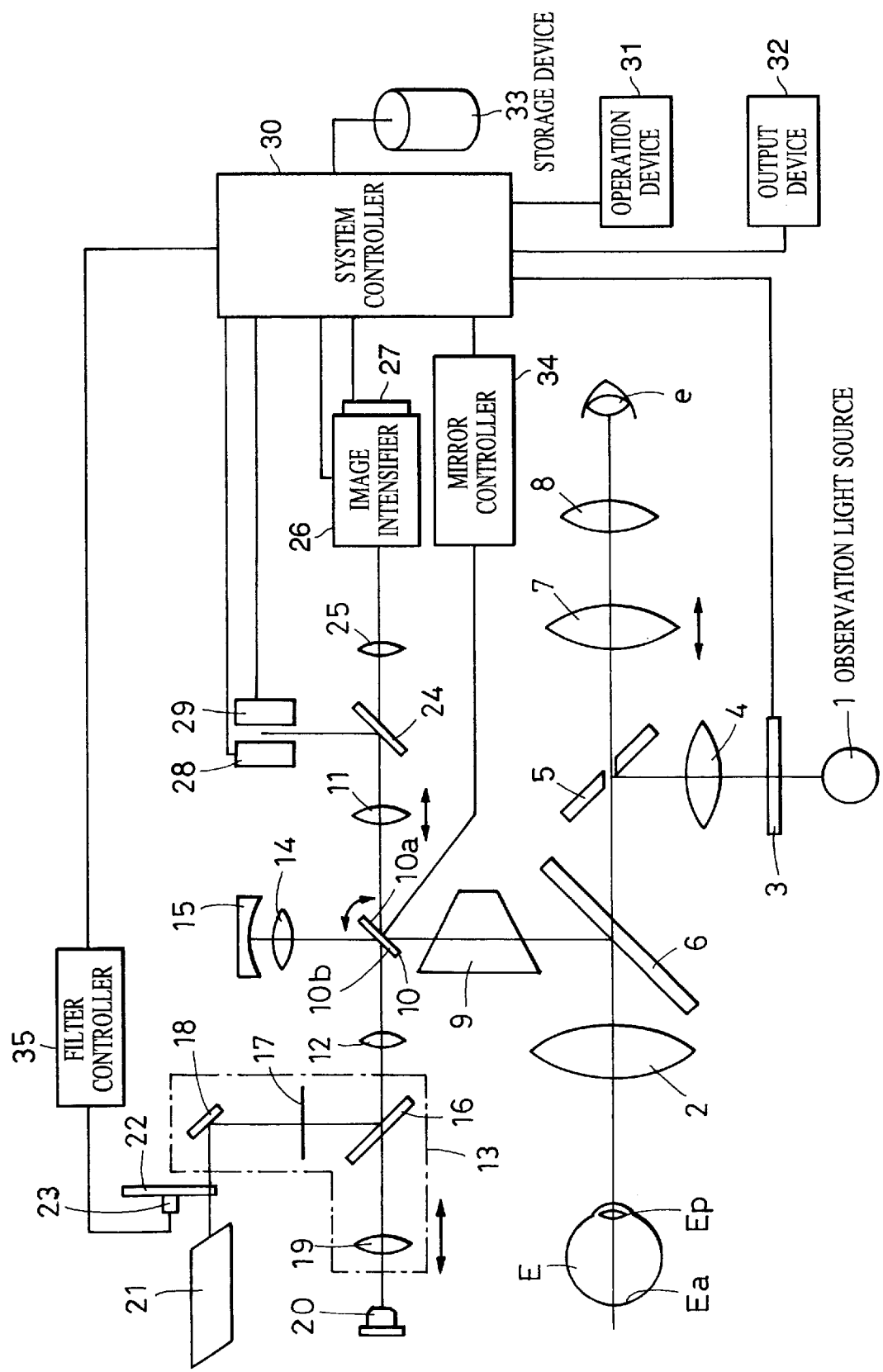
FIG. 1 is a schematic diagram illustrating an embodiment of the present invention.

FIG. 1 is a block diagram illustrating a retinal flow meter according to an embodiment of the present invention. On an illumination optical path from an observation light source 1, such as a tungsten lamp, which emits white light, to an objective lens 2, which faces a patient's eye E, a transmitting-type liquid crystal panel 3 for displaying a fixation point, which is in an optically conjugate position with an eye fundus Ea of the patient's eye E and which is movable along the optical path, a relay lens 4, an apertured mirror 5, and a band-pass mirror 6, which transmits yellow-range wavelength light and reflects most of the other ranges of light, are sequentially disposed. Behind the apertured mirror 5, an eye fundus observation system, which is formed of an image forming lens 7, which is movable along the optical path, and an eyepiece 8, is sequentially disposed before an operator's eye "e".

On the optical path in the diversion direction of the band-pass mirror 6, an image rotator 9 and a galvanometric mirror 10 having both sides polished and having a rotational axis perpendicular to the plane of the drawing are provided. A relay lens 11, which is movable along the optical path is disposed in the reflecting direction of a lower reflecting surface 10a of the galvanometric mirror 10. A lens 12 and a focusing unit 13, which is movable along the optical path, are disposed in the reflecting direction of an upper reflecting surface 10b of the galvanometric mirror 10. The galvanometric mirror 10 has a slit at the lower portion-of the above-described rotational axis. The front focal plane of the lens 12 is in a conjugate position with a pupil Ep of the patient's eye E, and the galvanometric mirror 10 is placed on the front focal plane of the lens 12.

Behind the galvanometric mirror 10, a lens 14 and a concave mirror 15 are disposed, which form a relay optical system for guiding a beam of light that passes through the slit of the galvanometric mirror 10 without being reflected at the lower reflecting surface 10a to the upper reflecting surface 10b.

In the focusing unit 13, a dichroic mirror 16 is disposed on the same optical path as the lens 12, and a mask plate 17, having a rectangular diaphragm, and a mirror 18 are provided on the optical path in the reflecting direction of the dichroic mirror 16. A lens 19 is disposed on the optical path in the transmitting direction of the dichroic mirror 16. The focusing unit 13 can be integrally moved.

On the optical path in the direction of incidence of the lens 19, a collimated, coherent measurement light source 20, such as a laser diode which emits, for example, red light, is disposed. On the optical path in the direction of incidence of the mirror 18, a tracking light source 21, such as a helium neon laser which emits high luminance light, for example, green light, different from other light sources, and a neutral density (ND) filter unit 22, for controlling the intensity of the tracking light source 21, are disposed.

Figure 2:
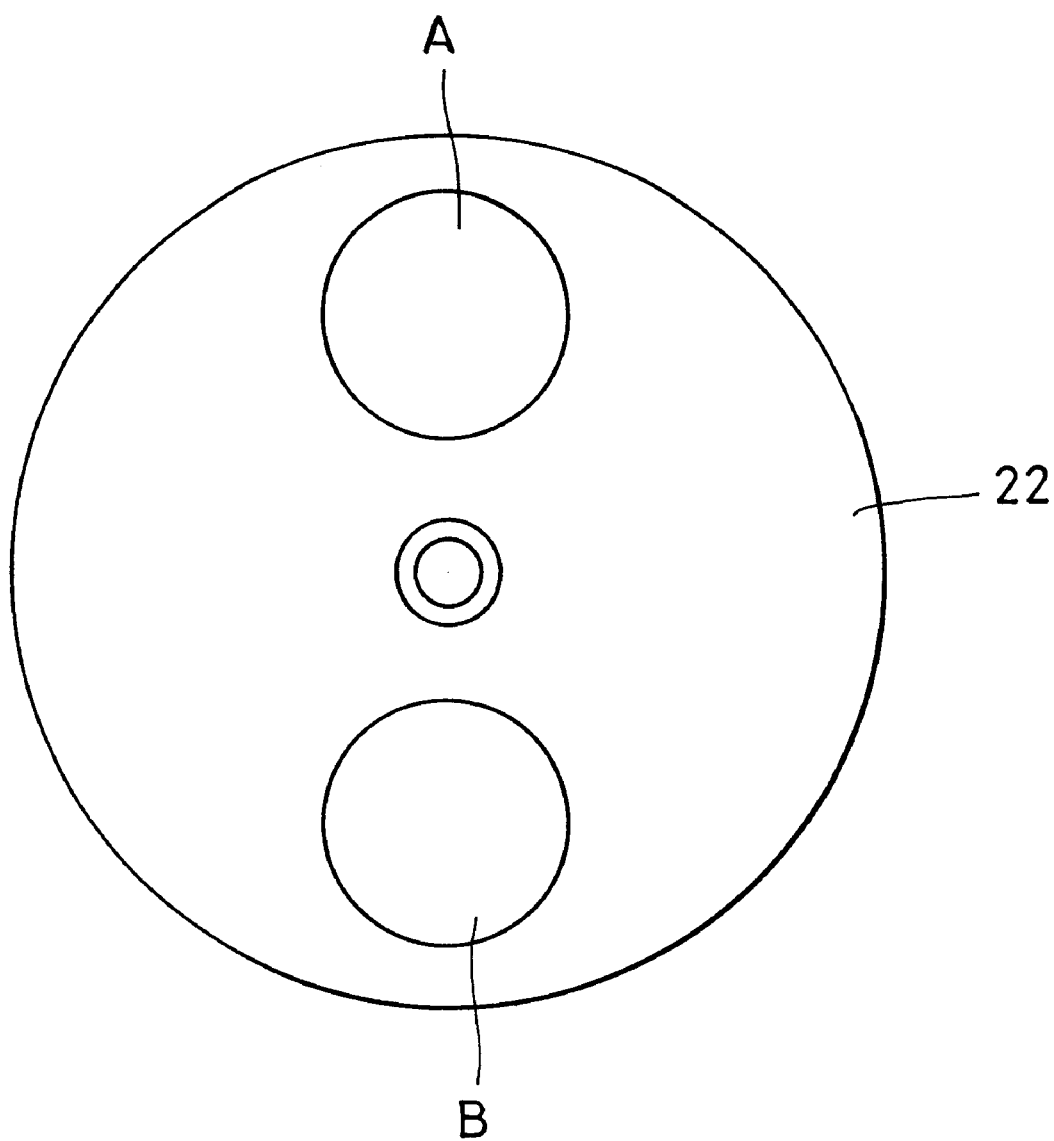
FIG. 2 is a front view illustrating a neutral density (ND) filter unit.

The ND filter unit 22 is formed of a plurality of ND filters whose transmittance is different, and is connected to a motor 23. By operating the motor 23, the ND filter to be inserted into the optical path is selected, thereby making it possible to control the intensity (quantity) of light to be applied to the patient's eye E from the tracking light source 21. FIG. 2 is a front view of the ND filter unit 22 provided with two ND filters A and B.

On the optical path of the reflecting direction of the lower reflecting surface 10a of the galvanometric mirror 10, the relay lens 11, a dichroic mirror 24, a magnifying lens 25, an image intensifier 26, which is an example of an optical amplifier, and a linear CCD 27 are sequentially disposed so as to form a blood-vessel detection system. Photomultipliers 28 and 29 are located in the reflecting direction of the dichroic mirror 24 so as to form a measurement light-receiving system. Although all the optical paths are shown on the same plane for ease of representation, the reflecting direction of the dichroic mirror 24 is perpendicular to the plane of the drawing.

A system controller 30 is provided for controlling the overall blood flow meter and also for performing calculations for measurements. The system controller 30 is electrically connected to an operation device 31 actuated by an operator, an output device 32, such as a display device or a printer for displaying or printing a measurement result, a storage device 33, outputs of the photomultipliers 28 and 29, an output of the image intensifier 26, and an output of the linear CCD 27. An output of the system controller 30 is electrically connected to a mirror controller 34 for controlling the galvanometric mirror 10 and to a filter controller 35 for controlling the transmittance of the ND filters. An output of the system controller 30 is also electrically connected to the image intensifier 26 so as to change the amplification factor of the image intensifier 26. The system controller 30 integrates, a processor for executing a program for calculating the blood-flow velocity by analyzing frequencies of the signals generated by the photomultipliers 28 and 29. The program executed by the processor of the system controller 30 also instructs the system controller to perform the steps illustrated in FIGS. 5 and 9 and discussed below. The program is stored in the system controller 30, but it is within the scope of the invention to store this program in any computer-readable medium, such as on floppy disc, a CD-ROM, a hard drive, a ROM, etc. The above-described liquid crystal panel 3, the image forming lens 7, the focusing unit 13, and the relay lens 11 are movable in the direction of the optical axis simultaneously in response to operating a focusing knob (not shown) so that the eye fundus Ea of the patient's eye E is constantly and optically conjugate with the liquid crystal panel 3, the eye fundus of the operator's eye "e", the mask plate 17, and the light-receiving surface of the image intensifier 26.

Figure 3:
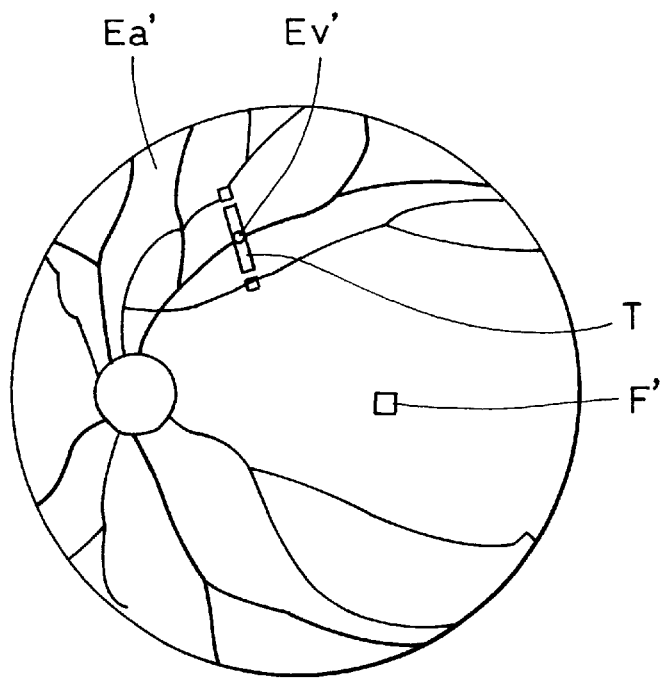
FIG. 3 illustrates an observation eye fundus image.
Figure 4:
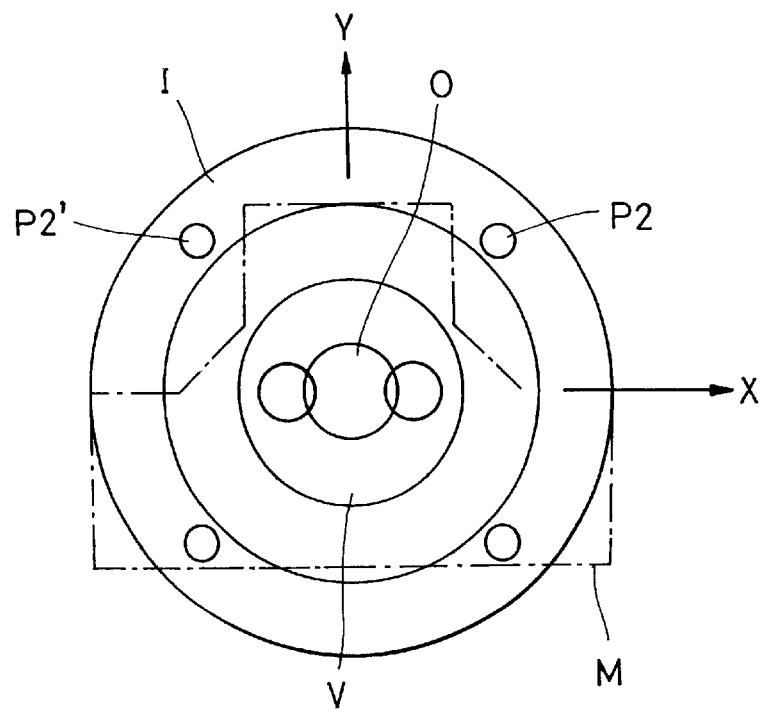
FIG. 4 illustrates beams of light formed on the pupil of a patient's eye.

Light emitted from each light source is applied to the patient's eye E, and the light reflected and scattered by the patient's eye E is guided to the operator, the photomultipliers 28 and 29, or the light-receiving surface of the image intensifier 26. More specifically, white light emitted from the observation light source 1 illuminates the liquid crystal panel 3 from behind, passes through the relay lens 4, and is reflected by the apertured mirror 5. The band-pass mirror 6 transmits only yellow-range wavelength light, which then passes through the objective lens 2 and temporarily forms an image on the pupil Ep of the patient's eye E as an eye fundus illumination light image I, as seen in FIG. 4. Then, the light almost uniformly illuminates the eye fundus Ea. Simultaneously, a fixation target F is displayed on the liquid crystal panel 3. The fixation target F is projected on the eye fundus Ea of the patient's eye E by illumination light, and is presented to the patient's eye E as a fixation target image F', as shown in FIG. 3.

The light reflected by the eye fundus Ea returns via the same optical path, and is extracted as a beam of light O for observing the eye fundus Ea from the pupil Ep, as shown in FIG. 4. The light O then passes through the opening at the center of the apertured mirror 5 and the image forming lens 7, and an eye fundus image Ea' can be observed by the operator's eye "e" via the eyepiece lens 8, as seen in FIG. 3. The operator performs alignment of the flow meter while observing the eye fundus image Ea' via the eyepiece lens 8.

The collimated measuring light emitted from the measurement light source 20 passes through the lens 19 and the dichroic mirror 16. The tracking light emitted from the tracking light source 21 is reflected by the mirror 18 and is shaped into a desired configuration by the mask plate 17. Then, the tracking light is reflected by the dichroic mirror 16 and is then superimposed on the above-described measuring light. In this case, the measuring light forms a spot image which is in conjugate position with the opening at the center of the mask plate 17 by the lens 19. The superimposed measuring light and the tracking light pass through the lens 12 and are reflected by the upper reflecting surface 10b of the galvanometric mirror 10. After passing through the lens 14, the measuring light and the tracking light are reflected by the concave mirror 15, pass through the lens 14 once again, and then return to the galvanometric mirror 10.

The galvanometric mirror 10 is in a position conjugate with the pupil Ep of the patient's eye E. The concave mirror 15 and the lens 14 are concentrically disposed on the optical path, and are provided with a relay function of forming an image on the galvanometric mirror 10 with −1 times magnification. Accordingly, the measuring light and the tracking light reflected on the upper reflecting surface 10b of the galvanometric mirror 10 return to the slit of the galvanometric mirror 10 and are then directed to the image rotator 9 without being reflected by the galvanometric mirror 10. The measuring light and the tracking light pass through the image rotator 9, are deflected to the objective lens 2 by the band-pass mirror 6, and illuminate the eye fundus Ea of the patient's eye E via the objective lens 2.

In this manner, the measuring light and the tracking light are reflected on the upper reflecting surface 10b of the galvanometric mirror 10, and are again incident on the galvanometric mirror 10 later while being eccentric from the optical axis of the objective lens 2. Then, the measuring light and the tracking light form a spot image P2 or P2' on the pupil Ep, as shown in FIG. 4, and illuminate the eye fundus Ea in a spot-like shape. Also, in FIG. 4, a region M surrounded by a one-dot chain line denotes the image of the lower reflecting surface 10a of the galvanometric mirror 10, O denotes the position of the beam of light for observing the eye fundus generated by the observation light source 1 and represents an image of the opening portion of the apertured mirror 5, and V denotes the position of the measuring light received from the target blood vessel, and represents an image of the effective portions of the upper and lower reflecting surfaces 10b and 10a of the galvanometric mirror 10.

The measuring light and the tracking light scattered and reflected by the eye fundus Ea are condensed by the objective lens 2, and most of the beams are reflected by the band-pass mirror 6. The reflected light then passes through the image rotator 9 and is reflected on the lower reflecting surface 10a of the galvanometric mirror 10. After passing through the relay lens 11, the light is separated into the measuring light and the tracking light by the dichroic mirror 24. The tracking light passes through the dichroic mirror 24, and is magnified by the magnifying lens 25 at a greater scale than the eye fundus image Ea' formed by the eye fundus observation optical system, thereby forming a blood-vessel image Ev' on the photoelectric surface of the image intensifier 26, as shown in FIG. 3. After being intensified, the blood-vessel image Ev' is captured on the linear CCD 27.

Meanwhile, the measuring light is reflected by the dichroic mirror 24, and is received by the photomultipliers 28 and 29, which generate received-light signals in response to receiving the measuring light. The received-light signals are output from the photomultipliers 28 and 29 and are input into the system controller 30, and based on the received-light signals, the processor of the system controller 30 determines the blood velocity of the blood vessel of the eye fundus Ea by analyzing the frequencies of the received-light signals according to the foregoing equation (1).

The light scattered and reflected by the eye fundus Ea, which is condensed by the objective lens 2 and passes through the band-pass mirror 6, is partially directed to the operator's eye "e" via the same optical path as the light scattered and reflected by the eye fundus Ea from the light from the observation light source 1, and can be observed by the operator as a tracking target image T shown in FIG. 3 and a measuring light image together with the eye fundus image Ea'.

Figure 5:
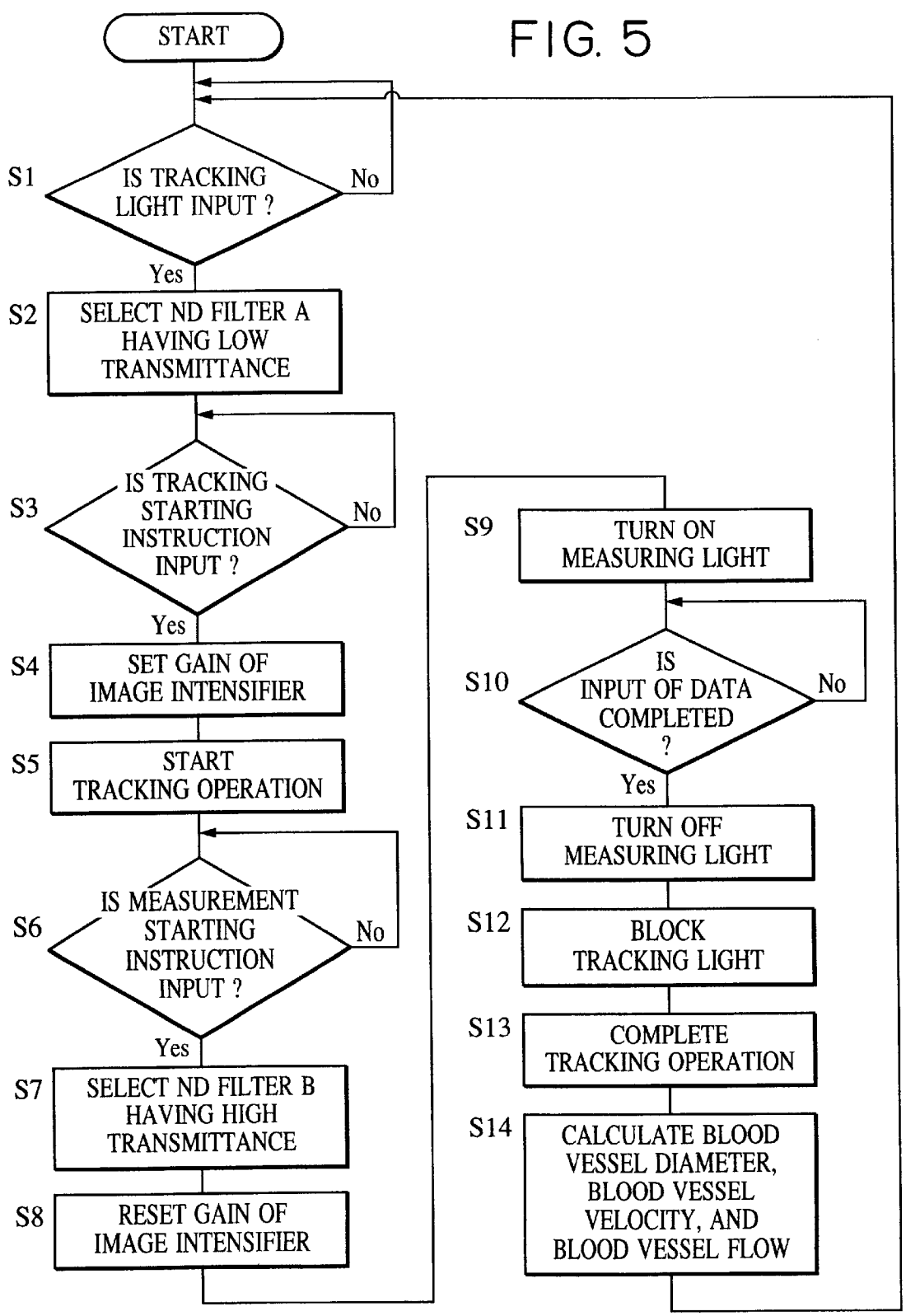
FIG. 5 is a flow chart illustrating the operation of the first embodiment.

FIG. 5 is a flow chart illustrating the control operation performed by the system controller 30. The operator first actuates an operation stick (not shown) so as to align the optical axis of the patient's eye E with the optical axis of the objective lens 2. The operator then brings the eye fundus Ea into focus by operating the above-described focusing knob (not shown) while observing the eye fundus image Ea'. Then, as discussed above, the fixation target F on the liquid crystal panel 3 comes into an optically conjugate position with the eye fundus Ea, and is presented to the patient's eye E. Accordingly, when the patient fixes his/her viewpoint on the fixation target image F' shown in FIG. 3, the operator is able to observe the eye fundus image Ea' shown in FIG. 3. Then, the operator moves the fixation target F by actuating the operation device 31 so as to guide the patient's eye E. As a result, a first subject portion can be fixed substantially at the center of the view field of the objective lens 8.

Then, the operator applies the tracking light to the eye fundus Ea by actuating the operation device 31. The operator also actuates a rotation operation knob (not shown) so that the tracking target image T is perpendicular to a first subject blood vessel, and controls the angle of the galvanometric mirror 10 so as to apply the measuring light to the first subject blood vessel.

As discussed above, after applying the tracking light to the blood vessel Ev, an image is formed on the photoelectric surface of the image intensifier 26 as the blood-vessel image Ev'. After being amplified, the blood-vessel image Ev' is then captured on the linear CCD 27, and is output as a blood-vessel-image signal. Then, the control operation of the system controller 30 shown in FIG. 5 is started. In step S1, the system controller 30 first determines whether the tracking light is input. If the outcome of step S1 is no, step S1 is repeated until the tracking light is input. If the result of step S1 is yes, the process proceeds to step S2. In step S2, the system controller 30 instructs the filter controller 35 to select the ND filter A having low transmittance so as to insert it into the optical path of the tracking light source 21. In response to this instruction, the filter controller 35 drives the motor 23 to insert the ND filter A into the optical path.

After determining the subject portion, the operator actuates the operation device 31 once again to input an instruction to start the tracking operation. Then, a signal output from the linear CCD 27 is input into the system controller 30. The system controller 30 then determines in step S3 whether an instruction to start the tracking operation is input. If the outcome of step S3 is no, the system controller 30 waits until the instruction is input. When it is found in step S3 that the tracking starting instruction is input, the process proceeds to step S4 in which the system controller 30 determines the amplification factor of the image intensifier 26 so that a suitable blood-vessel image Ev' can be captured by the linear CCD 27. Then, in step S5, based on the blood-vessel image Ev' captured by the linear CCD 27, the system controller 30 calculates data indicating the amount of movement of the blood-vessel image Ev', and outputs the blood-vessel image Ev' and the data indicating the amount of movement to the mirror controller 34. In response, the mirror controller 34 drives the galvanometric mirror 10 so as to compensate for the movement of the blood-vessel image Ev', thereby performing the tracking operation on the subject blood vessel.

After the tracking operation is stabilized to produce a stable and stationary blood-vessel image, the operator actuates the operation device 31 once again to input an instruction to start the blood-velocity the measurement operation. The system controller 30 then determines in step S6 whether the measurement starting instruction is input. If the result of step S6 is no, the system controller 30 waits until the instruction is input. When the instruction is input in step S6, the process proceeds to step S7. In step S7, the system controller 30 instructs the filter controller 35 to select the ND filter B having high transmittance so as to insert it into the optical path. In response to the instruction, the filter controller 35 drives the motor 23 to place the ND filter B into the optical path, and in step S8, the system controller 30 resets the amplification factor of the image intensifier 26 so as to prevent saturation of the blood-vessel image captured by and output from the linear CCD 27.

In this case, the intensity of the reflection from the eye fundus Ea is increased due to the high transmittance of the ND filter B input into the optical path. Thus, the system controller 30 reduces the amplification factor of the image intensifier 26. Subsequently, in step S9, the system controller 30 drives the measurement light source 20 to emit measuring light so as to receive signals representing the blood-vessel image from the linear CCD 27 and the Doppler signal from the photomultipliers 28 and 29.

The system controller 30 determines in step S10 whether the input of the blood-vessel image and the Doppler signal into the system controller 30 is completed. If the outcome of step S10 is no, the system controller 30 waits until the input of the data is completed. If the result of step S10 is yes, the process proceeds to step S11 in which the system controller 30 turns off the measurement light source 20. Then, in step S12, the system controller 30 instructs the filter controller 35 to insert the light-shielding portion without an ND filter into the optical path. In response to this instruction, the filter controller 35 drives the motor 23 to block light from tracking light source 21 from falling on mirror 18.

Accordingly, the application of the tracking light to the patient's eye E is stopped. Then, in step S13, the tracking operation is completed. In step S14, the system controller 30 calculates the blood-vessel diameter and the blood velocity, and also determines the blood-flow amount from the blood-vessel diameter and the blood velocity, thereby completing the measurement operation.

Figure 6A:
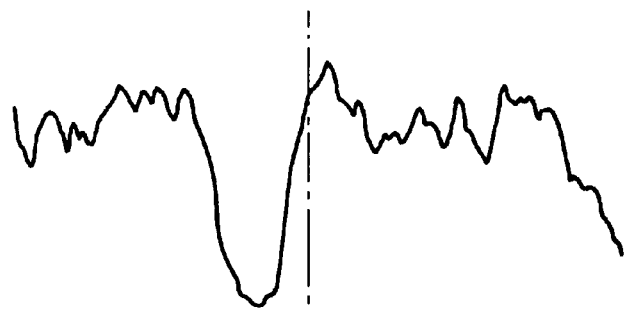
FIGS. 6A–6D illustrate the waveforms of blood-vessel-image signals.

After applying the tracking light to the blood vessel Ev, as shown in FIG. 3, the blood-vessel image Ev' is formed on the photoelectric surface of the image intensifier 26. After being amplified, the blood-vessel image Ev' is captured on the linear CCD 27. When the ND filter B having high transmittance is placed in the optical path of the tracking light source 21, which reduces the gain of the image intensifier 26, a blood-vessel-image signal having a good S/N ratio, such as that indicated by FIG. 6A, is output from the linear CCD 27. In FIGS. 6A–6D and 7A–7D the horizontal axis represents time and the vertical axis represents amplitude. On the other hand, when the ND filter A having low transmittance is placed in the optical path, which increases the gain of the image intensifier 26, a blood-vessel-image signal having a poor S/N ratio, such as that indicated by FIG. 6C, is output from the linear CCD 27, where the great thickness of the graph represents a poor S/N ratio.

Figure 6B:
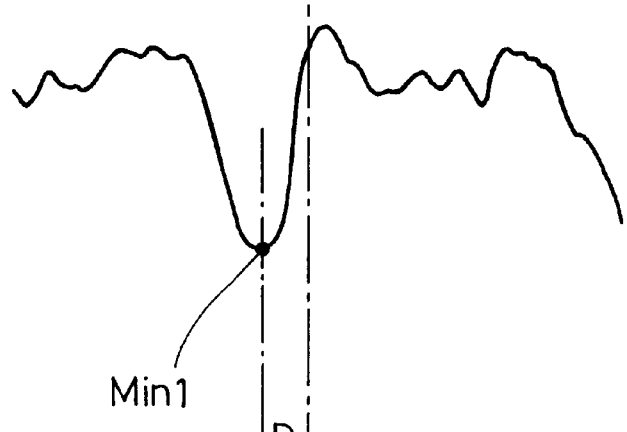
Figure 6C:
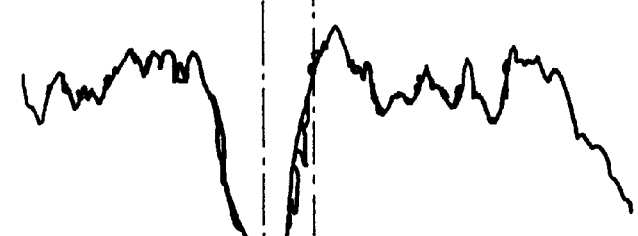
Figure 6D:
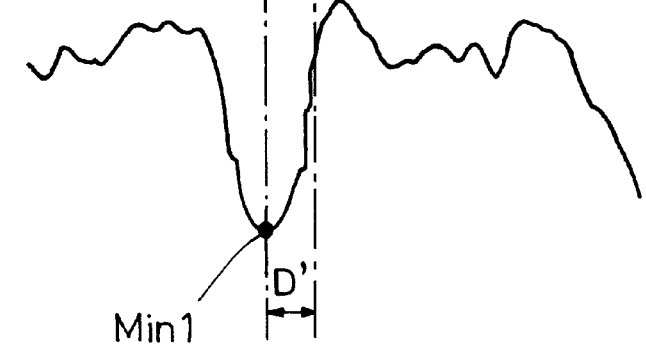

The blood-vessel-image signals indicated by FIGS. 6A and 6C are subjected by the system controller 30 to filtering processing without impairing the information on the blood vessel, and the resulting signals are indicated by FIGS. 6B and 6D, respectively. From these signal waveforms, the darkest point Min1 is detected and is calculated as information indicating the central position of the blood vessel. Then, the system controller 30 determines the difference D or D' between the blood-vessel central position and the tracking central position to which the measuring light is applied as the amount of movement of the blood vessel Ev.

During the tracking operation, it is only necessary to detect the information of the blood-vessel central position from the blood-vessel-image signal. Accordingly, FIGS. 6B and 6D show that the amounts of movement D and D' become almost the same without being influenced by the transmittance of the ND filter.

When calculating the blood-vessel diameter, in addition to the information of the blood-vessel central position Min1, as shown in FIGS. 7A–7D, the boundary points Max1 and Max2 between the blood vessels and peripheral tissue are detected by the system controller 30. From these three points, the half-width of (Min1–Max1) and (Min1–Max2) is calculated by the system controller 30, and is then corrected by the system controller 30 by using magnification of the flow meter, the refractive index of the eyeball, and the visual axis length of the ocular examination system, thereby determining the blood-vessel diameter.

Figure 7A:
FIGS. 7A–7D illustrate the waveforms of blood-vessel-image signals.

As discussed above, when the ND filter B having high transmittance is located in the optical path of the tracking light source 21, which reduces the gain of the image intensifier 26, a blood-vessel-image signal having a good S/N ratio, such as that indicated by FIG. 7A, is obtained. In contrast, when the ND filter A having low transmittance is located on the optical path of the tracking light source 21, which increases the gain of the image intensifier 26, a blood-vessel image having a poor S/N ratio is output, such as that indicated by FIG. 7C.

Figure 7B:
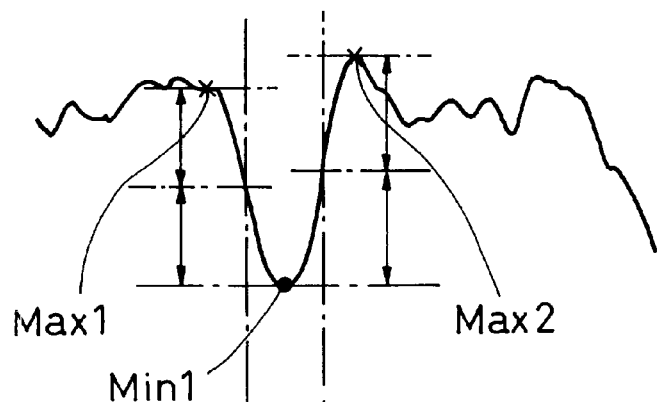
Figure 7C:
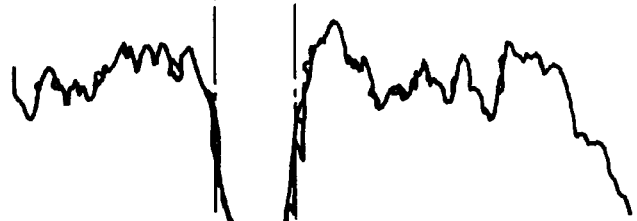
Figure 7D:
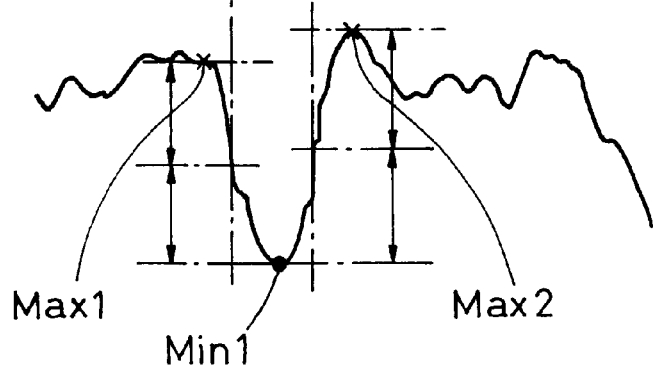

As in the tracking operation, the blood-vessel images indicated by FIGS. 7A and 7C are subjected to filtering processing by the system controller 30, and the resulting signals are represented in FIGS. 7B and 7D. From these signal waveforms, the half-widths Dia and Dia', which are required for determining the blood-vessel diameter, are calculated by the system controller 30 according to the above-described technique. Then, as indicated by FIGS. 7B and 7D, Dia' becomes greater than Dia due to the influence of noise. That is, the measurement values of the blood-vessel diameter and the blood velocity disadvantageously vary according to the transmittance of the ND filter.

Figure 8:
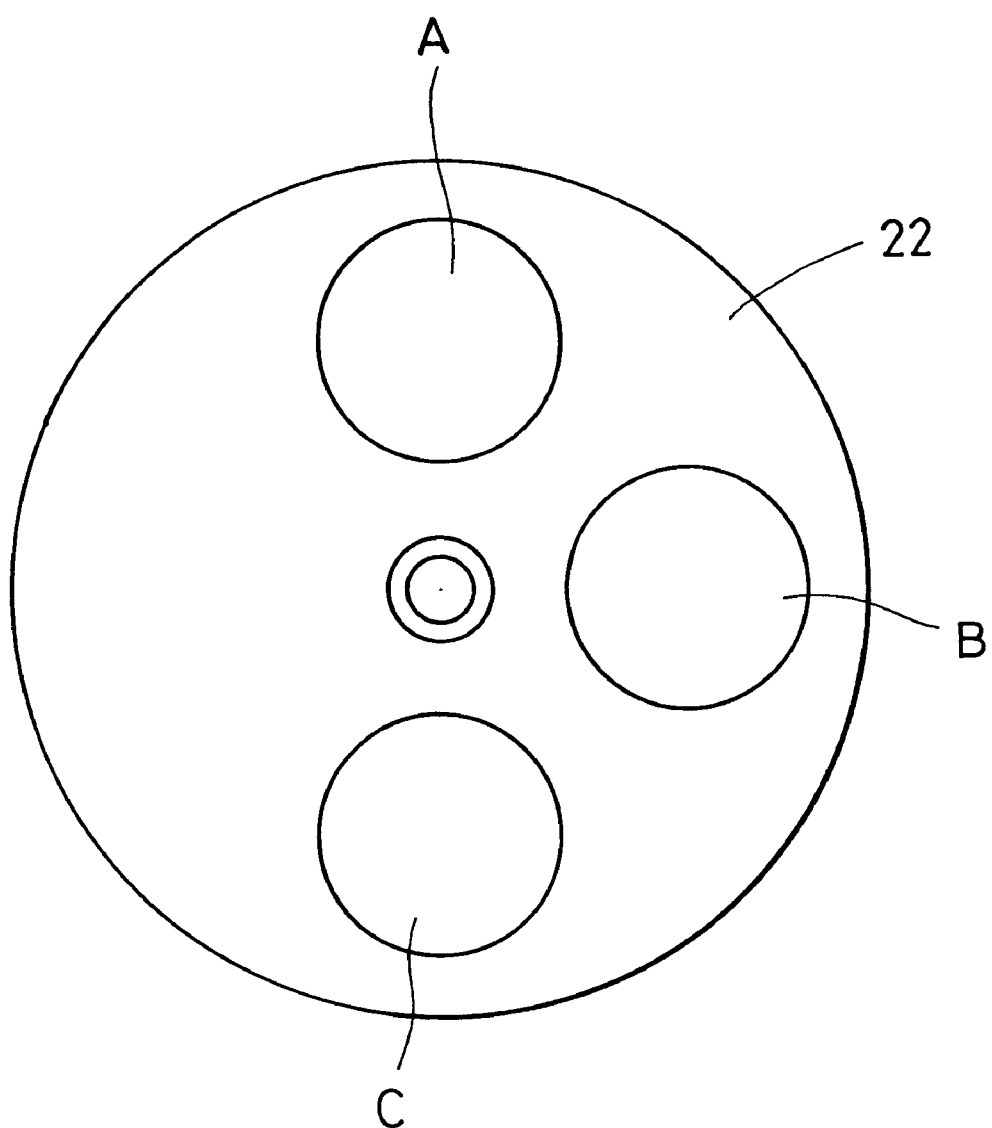
FIG. 8 is a front view illustrating an ND filter unit of a modification made to the first embodiment.

In this embodiment, two types of ND filers A and B are used for the ND filter unit 22. However, three types of ND filters A, B, and C whose transmittance is different, as shown in FIG. 8, or more types of ND filters, may be used, thereby making it possible to determine the blood-vessel diameter with a smaller error. Additionally, a suitable combination of the transmittance of the ND filter and the amplification factor of the image intensifier 26 is selected so that the intensify of the tracking light applied to the eye fundus Ea is minimized, thereby increasing the number of measurements.

In a modification to the first embodiment, the three types of ND filters shown in FIG. 8 may be used, and the transmittance of the ND filter may be increased in the order of the following three states 1, 2, and 3 so as to progressively increase the intensity of light applied to the eye fundus Ea:

1. the alignment state before starting the tracking operation;
2. the tracking state; and
3. the measurement state in which the blood-vessel diameter is measured while performing the tracking operation.

In state 1, the tracking light is used only for enabling the operator to perform alignment of the flow meter so that the measuring light can be applied to the subject blood vessel, and signal processing using a blood-vessel image output from the linear CCD 27 is not performed. Accordingly, the brightness of the tracking light applied to the eye fundus Ea is sufficient to enable the operator to visually check the eye fundus Ea. Thus, the intensity of the light can be set to a minimal level.

In state 2, the operator-has to detect the positional information of the subject blood vessel by using the blood-vessel image output from the linear CCD 27. Accordingly, the intensity of the tracking light applied to the eye fundus Ea must be raised to a greater level than that set in state 1.

In state 3, the intensity of the tracking light must be further increased to a greater level than that set in state 2.

The operation performed by the system controller 30 when using the ND filter unit 22 shown in FIG. 8 according to the above-described modification is discussed below with reference to the flow chart of FIG. 9. The operator actuates the operation device 31. Then, in step S1, the system controller 30 first determines whether tracking light is input. Then, in step S2, the system controller 30 instructs the filter controller 35 to select the ND filter A having the lowest transmittance so as to insert it into the optical path of the tracking light source 21. In response to this instruction, the filter controller 35 drives the motor 23 to insert the ND filter A into the optical path of the tracking light source 21. This state is equivalent to the alignment state 1 before starting the tracking operation.

After determining the subject portion of the eye to be examined, the operator actuates the operation device 31 to input a tracking starting instruction, and a signal output from the linear CCD 27 is input into the system controller 30. Then, the system controller 30 determines in step S3 whether a tracking starting instruction is input. If it has not been input, the system controller 30 awaits for its input. If the outcome of step S3 is yes, the process proceeds to step S4. In step S4, the system controller 30 instructs the filter controller 35 to select the ND filter B having the second lowest transmittance so as to insert it into the optical path. In response to this instruction, the filter controller 35 drives the motor 23 to insert the ND filter B into the optical path of the tracking light source 21.

Then, in step S5, the system controller 30 sets the amplification factor of the image intensifier 26 so that a suitable blood-vessel image Ev' can be captured on the linear CCD 27. In step S6, based on the blood-vessel image Ev', the system controller 30 calculates data indicating the amount of movement of the blood-vessel image Ev', and outputs the blood-vessel image Ev' and the information of the amount of movement to the mirror controller 34. The mirror controller 34 then drives the galvanometric mirror 10 to compensate for the amount of movement so that the blood-vessel image is stationary on the photomultipliers 28 and 29 and on the CCD 27, thereby tracking the blood vessel. This state is equivalent to the tracking state 2.

After the tracking operation is performed and the location of the blood-vessel image is stabilized, the system controller 30 actuates the operation device 31 once again to input a measurement starting instruction. The system controller 30 then determines in step S7 whether a measurement starting instruction is input. If the result of step S7 is yes, the process proceeds to step S8. In step S8, the system controller 30 instructs the filter controller 35 to select the ND filter C having the highest transmittance to insert it into the optical path. In response to this instruction, the filter controller 35 drives the motor 23 to insert the ND filter C into the optical path of the tracking light source 21.

When the ND filter C is inserted into the optical path, in step S9, the system controller. 30 resets the amplification factor of the image intensifier 26 so as to prevent saturation of a blood-vessel image captured by and output from the linear CCD 27. The system controller 30 receives the blood-vessel image and the data of the amount of movement required for calculating the blood-vessel diameter from the linear CCD 27. In this case, with the high transmittance of the ND filter disposed on the optical path, the intensity of the reflection from the eye fundus Ea increases. Accordingly, the amplification factor of the image intensifier 26 should be decreased. This state is equivalent to the measurement state 3 in which the blood-vssel diameter is measured while performing the tracking operation.

The system controller 30 then determines in step S10 whether the input of the blood-vessel image and the data of the amount of movement is completed. If not, the system controller 30 awaits completion of the input of this data. If the outcome of step S10 is yes, the process proceeds to step S11. In step S11, the system controller 30 instructs the filter controller 35 to select the ND filter B having the second low transmittance once again so as to insert it into the optical path. In response to this instruction, the filter controller 35 drives the motor 23 to insert the ND filter B into the optical path of the tracking light source 21.

In step S12, the system controller 30 resets the amplification factor of the image intensifier 26 so that a suitable blood-vessel-image Ev' can be captured on the linear CCD 27. Subsequently, in step S13, the system controller 30 turns on the measurement light source 20 so that photomultipliers 28 and 29 receive measuring light and generate received-light signals that are input into the system controller 30 as measurement data. This state is equivalent to the tracking state 2.

The system controller 30 then determines in step S14 whether the input of the data from the photomultipliers 28 and 29 and the linear CCD 27 is completed. If not, the system controller 30 awaits completion of the input of this data. If the result of step S14 is yes, the process proceeds to step S15 in which the system controller 30 instructs the turning off of the measurement light source 20. Then, in step S16, the system controller 30 instructs the filter controller 35 to insert the light-shielding portion without an ND filter into the optical path of the tracking light source 21. In response to this instruction, the filter controller 35 drives the motor 23 to insert the light-shielding portion into the optical path of the tracking light source 21. Accordingly, the tracking light is no longer applied to the patient's eye E. Then, in step S17, the tracking operation is completed. In step S18, the system controller 30 calculates the blood-vssel diameter and the blood velocity, and determines the blood-flow amount based on the blood-vessel diameter and the blood velocity. Then, the measurement operation is completed.

In the above-described embodiment and modification, the input into the system controller 30 of the data from the photomultipliers 28 and 29 and the input of the data from the linear CCD 27 are not performed simultaneously, and the transmittance of the ND filter is changed for each input operation. However, both data can be input into the system controller 30 simultaneously.

In the aforementioned embodiment and modification, the intensity of the laser light applied to the eye fundus Ea is controlled by the ND filter. However, the intensity of the laser light itself output from the laser light source may be electrically controlled.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An ocular examination system comprising:

an illumination system configured to illuminate a region of an eye fundus of an eye including a target blood vessel, said illumination system being configured to adjust the intensity of light illuminating the region;

an image pickup device positioned and configured to receive light scattered from the region illuminated by said illumination system and to produce signals in response to receiving the scattered light from the region;

a control system connected to said illumination system and said image pickup device so as to receive the signals produced by said image pickup device and configured to compute the diameter of the target blood vessel based on the signals from said image pickup device; and a tracking system connected to said control system and configured to perform an automatic tracking operation on the target blood vessel based on the signals from said image pickup device, wherein said control system is configured to control said tracking system so that said tracking system performs the automatic tracking operation simultaneous with said control system computing the diameter of the target blood vessel and so that said tracking system performs the automatic tracking operation when said control system does not computer the diameter of the target blood vessel, and wherein said control system is configured to control said illumination system to change the intensity of the illumination applied to the region when the automatic tracking operation and the target-blood-vessel-diameter computation are simultaneously performed above the level of the illumination applied to the region when the automatic tracking operation is performed while said control system does not compute the target-blood-vessel diameter.

2. An ocular examination system according to claim 1, wherein said illumination system comprises:

a light source of illumination light illuminating the region;

a plurality of filters of different transmittances that adjust the intensity of the illumination light illuminating the region; and a motor, connected to the plurality of filters, that moves one filter at a time into a path of the illumination light directed to the eye fundus, wherein said control system comprises:
a filter controller configured to control said motor to move one of the plurality of filters into the path of the illumination light to adjust the intensity of illumination light illuminating the region; and
a system controller connected to said filter controller, said tracking system, and said image pickup device and configured to compute the diameter of the target blood vessel, wherein said system controller controls said tracking system and controls said filter controller.

3. An ocular examination system according to claim 2, further comprising a neutral density unit comprising a circular element comprising:
said plurality of filters, which are spaced apart; and
a light-shielding portion extending between said plurality of spaced-apart filters,
wherein said plurality of filters are neutral density filters, and
wherein said motor engages the center of said circular element to rotate said circular element.

4. An ocular examination system according to claim 1, wherein said illumination system comprises:
a measurement light source emitting measurement light illuminating the region; and
a tracking light source emitting tracking light illuminating the region, wherein said illumination system adjusts the intensity of tracking light illuminating the region,
wherein said image pickup device comprises:
a measurement-light image pickup device positioned and configured to receive measurement light scattered by the region and configured to produce measurement-light signals; and
a tracking-light image pickup device positioned and configured to receive tracking light scattered by the region and configured to produce tracking-light signals;
wherein said control system is connected to said measurement-light image pickup device and said tracking-light image pickup device to receive the measurement-light signals and the tracking-light signals.

5. An ocular examination system according to claim 4, wherein said measurement light source comprises a laser diode emitting red light;
wherein said tracking light source comprises a helium neon laser emitting green light;
wherein said measurement-light image pickup device comprises two photomultipliers; and
wherein said tracking-light image pickup device comprises charge coupled device.

6. An ocular examination system according to claim 5, further comprising:
a set of optical elements positioned and configured to mix the measurement light and the tracking light into a combined beam and to direct the combined beam to the region of the eye fundus and to direct the combined beam scattered by the region toward said measurement-light image pickup device and said tracking-light image pickup device;
an optical element positioned and configured to separate the measurement light and the tracking light of the combined beam scattered by the region;
an optical element positioned and configured to direct the separated measurement light to the measurement-light image pickup device, and
an optical element positioned and configured to direct the tracking light to the tracking-light image pickup device.

7. An ocular examination system according to claim 1, wherein said tracking system comprises:
a galvanometric mirror;
a mirror controller, connected to said galvanometric mirror and said control system,
wherein said control system controls said mirror controller,
wherein said image pickup device captures an image of the target blood vessel and produces a blood-vessel-image signal in response to capturing the image of the target blood vessel, and transmits the blood-vessel-image signal to said control system,
wherein said control system determines the amount of movement of the target blood-vessel image captured by said image pickup device over time from the blood-vessel-image signal received from said image pickup device, and
wherein said control system instructs said mirror controller to move said galvanometric mirror to produce a substantially stationary target blood-vessel image on said image pickup device in response to determining the amount of movement of the target blood-vessel image.

8. An ocular examination system according to claim 1, wherein said control system determines the amount of movement of the target blood vessel, and then determines the target blood vessel diameter, the velocity of blood flow in the target blood vessel, and the blood flow amount in the target blood vessel in response to receiving the signals produced by said image pickup device.

9. An ocular examination system according to claim 1, wherein said illumination system comprises:
a light source;
selectable neutral density filters positioned in an optical path between said light source and the eye fundus, wherein each neutral density filter has a different transmittance, and
a mechanism connected to said selectable neutral density filters,
wherein said mechanism selects one neutral density filter at a time to place in the optical path, thereby adjusting the intensity of light illuminating the region, and
wherein said control system controls said mechanism to select a desired neutral density filter to place in the optical path.

10. An ocular examination system according to claim 1, further comprising an intensifier disposed in front of said image pickup device,
wherein said intensifier is connected to said image pickup device and to said control system,
wherein said intensifier receives an image of the region,
wherein said intensifier optically amplifies the image of said region by an amplification factor, and
wherein said control system controls the amplification factor of said intensifier according to the intensity of the illumination of said illumination system.

11. An ocular examination system according to claim 10, wherein said control system reduces the amplification factor of said intensifier when increasing the intensity of illumination applied to the region, and
wherein said control system increases the amplification factor of said intensifier when decreasing the intensity of illumination applied to the region.

12. An ocular examination system according to claim 1, wherein said control system controls said illumination system to increase the intensity of the illumination when the automatic tracking operation is performed compared to the intensity of the illumination when the automatic tracking operation is not performed.

13. An ocular examination system according to claim 1,
wherein said control system controls said illumination system to illuminate the region with light of greater intensity when the automatic tracking operation and the target-blood-vessel diameter computation ate simultaneously performed than when the automatic tracking operation is performed and the target-blood-vessel diameter computation is not performed, and
wherein said control system controls said illumination system to illuminate the region with light of greater intensity when the automatic tracking operation is performed and the target-blood-vessel diameter computation is not performed than when neither the automatic tracking operation nor the target-blood-vessel diameter computation is performed.

14. An ocular examination system according to claim 1,
wherein said image pickup device captures an image of the target blood vessel and produces a blood-vessel-image signal in response to capturing the image of the target blood vessel, and transmits the blood-vessel-image signal to said control system,
wherein said control system determines the signal waveform of the blood-vessel-image signal,
wherein said control system determines the darkest point of the signal waveform as the blood vessel central position of the target blood vessel,
wherein said control system determines the tracking central position of the target blood vessel, the tracking central position being the central position of the light from said illumination system applied to the target blood vessel,
wherein said control system determines the difference between the blood vessel central position and the tracking central position, and
wherein said control system identifies the difference as the amount of movement of the target blood vessel.

15. An ocular examination system according to claim 14,
wherein the darkest point is denoted by Min1,
wherein said control system determines the boundary points Max1 and Max2 between the target blood vessel and peripheral tissue from the signal waveform,
wherein said control system determines the half widths Min1–Max1 and Min1–Max2, and
wherein said control system corrects the half widths by using any magnification produced of said ocular examination system, the refractive index of the eye, and the visual axis length of the ocular examination system to determine the target-blood-vessel diameter.

16. An ocular examination system according to claim 1,
wherein said illumination system outputs tracking light to the region and measuring light to the region,
wherein said image pickup device is configured and positioned to receive tracking light scattered by the region and produces tracking signals in response to receiving the tracking light scattered by the region,
wherein said image pickup device is configured and positioned to receive measuring light scattered by the region and produces measuring signals in response to receiving the measuring light scattered by the region,
wherein said illumination system comprises:
a first filter; and
a second filter,
wherein said first and second filters are insertable into the optical path of light illuminating the region to change the intensity of light illuminating the region,
wherein the transmittance of said first filter is lower than said second filter,
wherein said control system determines whether tracking signals are input thereinto from said image pickup device,
wherein said control system instructs said illumination system to insert said first filter into the optical path when said control system determines that tracking signals are input thereinto from said image pickup device,
wherein the tracking light scattered by the region forms a target blood-vessel image,
wherein said ocular examination system further comprises an image intensifier connected to said input pickup device and configured and positioned to receive the target blood-vessel image, to amplify the target blood-vssel image by an amplification factor, and to direct the amplified target blood vessel onto the image pickup device,
wherein said control system determines the amplification factor of said image intensifier to be used with said first filter,
wherein said control system determines the amount of movement of the target blood vessel based on the target signals from said image pickup device after determining the amplification factor of said image intensifier,
wherein said control system controls said tracking system to perform automatic tracking of the target blood vessel in response to determining the amount of movement of the target blood vessel so that the target blood-vessel image, amplified by said image intensifier, is stationary on said input pickup device,
wherein said control system instructs said illumination system to remove said first filter from the optical path and to insert said second filter into the optical path after said control system has controlled said tracking system to perform automatic tracking so that the target blood-vessel image is stationary on said input pickup device,
wherein said control system changes the amplification factor of said image intensifier after instructing said illumination system to remove said first filter and to insert said second filter into the optical path to prevent saturation of the target blood-vessel image captured by said image pickup device,
wherein said control system controls said illumination system to illuminate the region with measuring light so that said control system receives both tracking signals and measuring signals from said image pickup device after said control system changes the amplification factor,
wherein said control system calculates the target-blood-vessel diameter, the blood velocity, and the blood flow amount after receiving both tracking signals and measuring signals from said image pickup device.

17. An ocular examination.system according to claim 16,
wherein after said control system controls said illumination system to illuminate the region with measuring light, said control system determines whether the input of tracking signals and measuring signals is complete, wherein said control system stops said illumination system from illuminating the region with measuring light and tracking light after determining that the input of tracking signals and measuring signals is complete, and wherein said control system calculates the target-blood-vessel diameter, the blood velocity, and the blood flow amount after stopping said illumination system from illuminating the region with measuring light and tracking light.

18. An ocular examination system according to claim 1, wherein said illumination system outputs tracking light to the region and measuring light to the region, wherein said image pickup device is configured and positioned to receive tracking light scattered by the region and produces tracking signals in response to receiving the tracking light scattered by the region, wherein said image pickup device is configured and positioned to receive measuring light scattered by the region and produces measuring signals in response to receiving the measuring light scattered by the region, wherein said illumination system comprises:
  a first filter;
  a second filter; and
  a third filter,
  wherein said first, second, and third filters are insertable into the optical path of light illuminating the region to change the intensity of light illuminating the region, wherein the transmittance of said first filter is lower than said second filter, and the transmittance of said second filter is lower than said third filter, wherein said control system determines whether tracking signals are input thereinto from said image pickup device, wherein said control system instructs said illumination system to insert said first filter into the optical path when said control system determines that tracking signals are input thereinto from said image pickup device to permit an operator to align said ocular examination system with the eye before starting the automatic tracking operation, wherein the tracking light scattered by the region forms a target blood-vessel image and said image pickup device is configured and positioned to receive the target blood-vessel image and to produce target blood-vessel image data, wherein said ocular examination system further comprises an image intensifier connected to said input pickup device and configured and positioned to receive the target blood-vessel image, to amplify the target blood-vssel image by an amplification factor, and to direct the amplified target blood-vessel image onto the image pickup device, wherein said control system instructs said illumination system to remove said first filter from the optical path and to insert said second filter into the optical path in response to receiving a tracking starting instruction from the operator, wherein said control system determines the amplification factor of said image intensifier to be used with said second filter, wherein said control system determines the amount of movement of the target blood vessel based on the tracking signals from said image pickup device after determining the amplification factor of said image intensifier, wherein said control system controls said tracking system to perform automatic tracking of the target blood vessel in response to determining the amount of movement of target blood vessel so that the target blood-vessel image, amplified by said image intensifier, is stationary on said input pickup device, wherein said control system instructs said illumination system to remove said second filter from the optical path and to insert said third filter into the optical path after said control system has controlled said tracking system to perform automatic tracking so that the target blood-vessel image is stationary on said input pickup device, wherein said control system changes the amplification factor of said image intensifier after instructing said illumination system to remove said second filter and to insert said third filter into the optical path to prevent saturation of the target blood-vessel image captured by said image pickup device, wherein said control system determines whether the input of the target blood-vessel image data is complete and whether the tracking signal input from said image pickup device needed to compute the amount of movement of the target blood vessel is complete, wherein said control system controls said illumination system to remove said third filter from the optical path and to insert said second filter into the optical path after determining that the input of the target blood-vessel image data and the tracking-signal input is complete, wherein said control system changes the amplification factor of said image intensifier after instructing said illumination system to remove said third filter and to insert said second filter into the optical path, wherein said control system controls said illumination system to illuminate the region with measuring light so that said control system receives both tracking signals and measuring signals from said image pickup device after said control system changes the amplification factor after instructing said illumination system to remove said third filter and to insert said second filter into the optical path, and wherein said control system calculates the target-blood-vessel diameter, the blood velocity, and the blood flow amount after receiving both tracking signals and measuring signals from said image pickup device.

19. An ocular examination system comprising:

illumination means for illuminating a region of an eye fundus of an eye including a target blood vessel and for adjusting the intensity of light illuminating the region;

image pickup means for receiving light scattered from the region illuminated by said illumination means and for producing signals in response to receiving the scattered light from the region;

control means for computing the diameter of the target blood vessel based on the signals from said image pickup means; and tracking means for performing an automatic tracking operation on the target blood vessel based on the signals from said image pickup means, wherein said control means comprises:
  means for controlling said tracking means so that said tracking means performs the automatic tracking operation simultaneous with said control means computing the diameter of the target blood vessel and so that said tracking means performs the automatic tracking operation when said control means does not compute the diameter of the target blood vessel; and means for controlling said illumination means to change the intensity of the illumination applied to the region when the automatic tracking operation and the target-blood-vessel-diameter computation are simultaneously performed above the level of the illumination applied to the region when the automatic tracking operation is performed while said control means does not compute the target-blood-vssel diameter.

20. An ocular examination system according to claim 19, wherein said illumination means comprises:

light source means for producing illumination light illuminating the region;

a plurality of filter means for decreasing the intensity of the illumination light; and means for moving one filter means at a time into a path of the illumination light directed to the eye fundus, wherein said control means comprises:

filter-means control means for controlling said moving means to move one of the plurality of filter means into the path of the illumination light to adjust the intensity of illumination light illuminating the region; and system control means for computing the diameter of the target blood vessel and for controlling said tracking means and said filter-means control means.

21. An ocular examination system according to claim 20, wherein said plurality of filter means are neutral density filter means, said system further comprising:

means for housing said plurality of filter means in a spaced apart manner, said housing means comprising light-shielding means for shielding the eye from the illumination light from said light source means; and wherein said moving means moves said housing means to place one of said plurality of filter means or said light-shielding means in the optical path of illumination light from said light source means to the eye.

22. An ocular examination system according to claim 19, wherein said illumination means comprises:

measurement light source means for emitting measurement light illuminating the region; and tracking light source means for emitting tracking light illuminating the region, wherein said illumination means comprises means for adjusting the intensity of tracking light illuminating the region, wherein said image pickup means comprises:

measurement-light image pickup means for receiving measurement light scattered by the region and producing measurement-light signals; and tracking-light image pickup means for receiving tracking light scattered by the region and producing tracking-light signals;

wherein said control means comprises means for receiving, the measurement-light signals and the tracking-light signals.

23. An ocular examination system according to claim 22, wherein said measurement light source means comprises laser diode means for emitting red light, wherein said tracking light source means comprises a helium neon laser means for emitting green light, wherein said measurement-light image pickup means comprises first and second photomultiplier means for converting the measurement light to measurement light signals, and wherein said tracking-light image pickup means comprises charge coupled device means for converting the tracking light to tracking light signals.

24. An ocular examination system according to claim 23, further comprising:

means for mixing the measurement light and the tracking light into a combined beam, for directing the combined beam to the region of the eye fundus, and for directing the combined beam scattered by the region toward said measurement-light image pickup means and said tracking-light image pickup means;

means for separating the measurement light and the tracking light of the combined beam scattered by the region;

means for directing the separated measurement light to the measurement-light image pickup means, and means for directing the separated tracking light to the tracking-light image pickup means.

25. An ocular examination system according to claim 19, wherein said tracking means comprises:

rotatable mirror means for reflecting the tracking light and for rotating;

mirror control means for controlling the rotation of said rotatable mirror means, wherein said image pickup means comprises means for capturing an image of the target blood vessel, for producing a blood-vessel-image signal in response to capturing the image of the target blood vessel, and for transmitting the blood-vessel-image signal to said control means, wherein said control means further comprises:

means for determining the amount of movement of the target blood-vessel image captured by said image pickup means over time from the blood-vessel-image signal received from said image pickup means; and means for instructing said mirror control means to rotate said rotatable mirror means to produce a substantially stationary target blood-vessel image on said image pickup means in response to said determining means determining the amount of movement of the target blood-vssel image.

26. An ocular examination system according to claim 19, wherein said control means comprises means for determining the amount of movement of the target blood vessel, and then determining the target blood-vessel diameter, the velocity of blood flow in the target blood vessel, and the blood flow amount in the target blood vessel based on the signals produced by said image pickup means.

27. An ocular examination system according to claim 19, wherein said illumination means comprises:

light source means for emitting illumination light; and selectable neutral density filter means for reducing the intensity of the illumination light reaching the eye fundus from said light source means;

wherein each neutral density filter means has a different transmittance, and means for selecting one neutral density filter at a time to reduce the intensity of illumination light reaching the eye fundus from said light source means, wherein said control means controls said selecting means to select a desired neutral density filter means.

28. An ocular examination system according to claim 19, further comprising:
  means for forming an image of the region; and
  means for optically amplifying the image of the region by an amplification factor,
  wherein said image pickup means receives the amplified image and produces signals in response to receiving the amplified image, and
  wherein said control means comprises means for controlling the amplification factor of said optical amplifying means according to the intensity of the illumination of said illumination means.

29. An ocular examination system according to claim 28, wherein said control means comprises:
  means for reducing the amplification factor when said control means increases the intensity of illumination applied to the region; and
  means for increasing the amplification factor when said control means decreases the intensity of illumination applied to the region.

30. An ocular examination system according to claim 19, wherein said control means comprises means for controlling said illumination means to increase the intensity of the illumination when the automatic tracking operation is performed compared to the intensity of the illumination when the automatic tracking operation is not performed.

31. An ocular examination system according to claim 19, wherein said control means comprises:
  means for controlling said illumination means to illuminate the region with light of greater intensity when the automatic tracking operation and the target-blood-vessel diameter computation are simultaneously performed than when the automatic tracking operation is performed and the target-blood-vessel diameter computation is not performed; and
  means for controlling said illumination means to illuminate the region with light of greater intensity when the automatic tracking operation is performed and the target-blood-vessel diameter computation is not performed than when neither the automatic tracking operation nor the target-blood-vessel diameter computation is performed.

32. An ocular examination system according to claim 19, wherein said image pickup means comprises means for capturing an image of the target blood vessel and for producing a blood vessel image signal in response to capturing the image of the target blood vessel,
  wherein said control means comprises:
    means for determining the signal waveform of the blood vessel image signal,
    means for determining the darkest point of the signal waveform as the blood vessel central position of the target blood vessel,
    means for determining the tracking central position of the target blood vessel, the tracking central position being the central position of the light from said illumination means applied to the target blood vessel,
    means for determining the difference between the blood vessel central position and the tracking central position, and
    means for identifying the difference as the amount of movement of the target blood vessel.

33. An ocular examination system according to claim 32, wherein the darkest point is denoted by Min1,
  wherein said control means comprises:
    means for determining the boundary points Max1 and Max2 between the target blood vessel and peripheral tissue from the signal waveform,
    means for determining the half widths Min1–Max1 and Min1–Max2, and
    means for correcting the half widths by using any magnification produced of said ocular examination system, the refractive index of the eye, and the visual axis length of the ocular examination system to determine the target blood-vessel diameter.

34. An ocular examination system according to claim 19, wherein said illumination means comprises means for outputting tracking light to the region and measuring light to the region,
  wherein said image pickup means comprises:
    means for receiving tracking light scattered by the region and for producing tracking signals in response to receiving the tracking light scattered by the region; and
    means for receiving measuring light scattered by the region and for producing measuring signals in response to receiving the measuring light scattered by the region,
  wherein said illumination means further comprises:
    first filter means for reducing the intensity of the tracking light by a first amount; and
    second filter means for reducing the intensity of the tracking light by a second amount, smaller than the first amount,
  wherein said control means comprises:
    means for determining whether tracking signals are input into said control means thereinto from said image pickup means; and
    means for instructing said illumination means to use said first filter means to reduce the intensity of the tracking light when said determining means determines that tracking signals are input into said control means,
  wherein said ocular examination system further comprises:
    means for forming a target blood vessel image from tracking light scattered by the target blood vessel; and
    means for amplifying the target blood-vessel image by an amplification factor,
  wherein said image pickup means comprises means for producing tracking signals in response to receiving the amplified target blood-vessel image,
  wherein said control means further comprises:
    means for determining the amplification factor of said amplifying means to be used when said first filter means determines the intensity of the tracking light;
    means for determining the amount of movement of the target blood vessel based on the tracking signals from said image pickup device after the amplification factor to be used when said first filter means determines the intensity of the tracking light is determined;
    means for controlling said tracking means to perform automatic tracking of the target blood vessel in response to the determining of the amount of movement of the target blood vessel so that the target blood-vessel image, amplified by said amplifying means, is stationary on said input pickup means;

means for instructing said illumination means to use said second filter means to determine the intensity of the tracking light after said tracking means has been controlled to perform automatic tracking so that the target blood-vessel image is stationary on said input pickup means;

means for changing the amplification factor after said second filter is instructed to be used to determine the intensity of the tracking light to prevent saturation of the target blood-vessel image captured by said image pickup means;

means for controlling said illumination means to illuminate the region with measuring light so that said image pickup means produces both tracking signals and measuring signals after the amplification factor is changed; and means for calculating the target blood-vessel diameter, the blood velocity, and the blood flow amount based on both the tracking signals and measuring signals.

35. An ocular examination system according to claim 34, wherein said control means further comprises:

means for determining the completion of the production of the tracking signals and the measuring signals after said illumination means is controlled to illuminate the region with measuring light; and means for stopping said illumination means from illuminating the region with measuring light and tracking light after completion of the producing of the tracking signals and the measuring signals is determined;

wherein said means for calculating the target blood-vessel diameter, the blood velocity, and the blood flow amount based on both the tracking signals and measuring signals performs its calculating function after said stopping means stops said illumination means from illuminating the region with measuring light and tracking light.

36. An ocular examination system according to claim 19, wherein said illumination means comprises means for outputting tracking light to the region and measuring light to the region, wherein said image pickup means comprises:

means for receiving tracking light scattered by the region and for producing tracking signals in response to receiving the tracking light scattered by the region; and means for receiving measuring light scattered by the region and for producing measuring signals in response to receiving the measuring light scattered by the region, wherein said illumination means comprises:

first filter means for reducing the intensity of the tracking light by a first amount;

second filter means for reducing the intensity of the tracking light by a second amount, smaller than the first amount; and third filter means for reducing the intensity of the tracking light by a third amount, smaller than the second amount, wherein said ocular examination system further comprises:

means for forming a target blood-vessel image from the tracking light scattered by the region; and means for amplifying the intensity of the target blood-vessel image by an amplification factor, wherein said image pickup means further comprises means for receiving the amplified target blood-vessel image and for producing target blood-vessel image data in response to receiving the amplified target blood-vessel image data, wherein said control means comprises:

means for determining whether said control means receives the tracking signals;

means for instructing said illumination means to use said first filter means to reduce the intensity of the tracking light when said determining means determines that tracking signals are received by said control means to permit an operator to align said ocular examination system with the eye before starting the automatic tracking operation;

means for instructing said illumination means to use the second filter means to reduce the intensity of the tracking light in response to receiving a tracking starting instruction from the operator;

means for determining the amplification factor to be used when said second filter means is used to reduce the intensity of the tracking light;

means for determining the amount of movement of the target blood vessel based on the tracking signals after the determining of the amplification factor;

means for controlling said tracking means to perform automatic tracking of the target blood vessel in response to determining the amount of movement of the target blood vessel so that the amplified target blood-vessel image is stationary on said input pickup means;

means for instructing said illumination means to use said third filter means to reduce the intensity of the tracking light after said tracking means has been controlled to perform automatic tracking so that the amplified target blood-vessel image is stationary on said input pickup means;

means for changing the amplification factor to an amplification factor to be used when said third filter means is used to reduce the intensity of the tracking light to prevent saturation of the target blood-vessel image captured by said image pickup device;

means for determining whether the production of the target blood-vessel image data is complete and whether the production of the tracking-signal needed to compute the amount of movement of the target blood vessel is complete;

means for controlling said illumination means to use the second filter to reduce the intensity of the tracking light after a determination that the production of the target blood-vessel image data and the tracking signal is complete;

means for changing the amplification factor when said illumination means is controlled to use the second filter means to reduce the intensity of the tracking light;

means for controlling said illumination means to illuminate the region with measuring light so that said image pickup means produces both tracking signals and measuring signals after the amplification factor is changed when said illumination means is controlled to use the second filter means; and means for calculating the target blood-vessel diameter, the blood velocity, and the blood flow amount based on both the tracking light signals and the measuring signals.

* * * * *

UNITED STATES PATENT AND TRADEMARK OFFICE
CERTIFICATE OF CORRECTION

PATENT NO.    : 6,535,757 B2
DATED         : March 18, 2003
INVENTOR(S)   : Shigeaki Ono It is certified that error appears in the above-identified patent and that said Letters Patent is hereby corrected as shown below:

Column 1,
Line 30, "a" should read -- α --.

Column 2,
Line 54, "to,receive" should read -- to receive --.

Column 3,
Line 1, "neous" should read -- neously --.
Line 4, "computer" should read -- compute --.

Column 4,
Line 25, "portion-of" should read -- portion of --.

Column 5,
Line 20, "integrates," should read -- integrates --.

Column 8,
Line 13, "the" (2$^{nd}$ occurrence) should be deleted.

Column 11,
Line 14, "controller." should read -- controller --.

Column 12,
Line 45, "computer" should read -- compute --.

Column 18,
Line 65, "simultaneous" should read -- simultaneously --.

Column 20,
Line 19, "and means" should read -- and ¶ means --.

UNITED STATES PATENT AND TRADEMARK OFFICE
CERTIFICATE OF CORRECTION

PATENT NO.    : 6,535,757 B2
DATED         : March 18, 2003
INVENTOR(S)   : Shigeaki Ono It is certified that error appears in the above-identified patent and that said Letters Patent is hereby corrected as shown below:

<u>Column 22,</u>
Line 43, "blood vessel" should read -- blood-vessel --.

Signed and Sealed this

Twenty-eighth Day of October, 2003

JAMES E. ROGAN
*Director of the United States Patent and Trademark Office*